United States Patent [19]

Linhart et al.

[11] 4,200,743

[45] Apr. 29, 1980

[54] PREPARATION OF 1-CYANO-2,1,3-BENZOTHIADIAZINONES

[75] Inventors: Friedrich Linhart, Heidelberg; Gerd Stubenrauch, Ludwigshafen; Gerhard Hamprecht, Weinheim, all of Fed. Rep. of Germany

[73] Assignee: BASF Aktiengesellschaft, Fed. Rep. of Germany

[21] Appl. No.: 44,030

[22] Filed: May 31, 1979

[30] Foreign Application Priority Data

Jul. 24, 1978 [DE] Fed. Rep. of Germany ....... 2832404

[51] Int. Cl.² .......................................... C07D 285/16
[52] U.S. Cl. ..................................................... 544/11
[58] Field of Search .......................................... 544/11

[56] References Cited

U.S. PATENT DOCUMENTS 4,158,559  6/1979  Stubenrauch et al. ................. 544/11

FOREIGN PATENT DOCUMENTS 2656289  6/1978  Fed. Rep. of Germany .

*Primary Examiner*—John M. Ford
*Attorney, Agent, or Firm*—Keil & Witherspoon

[57] ABSTRACT

A process for the preparation of 1-cyano-2,1,3-benzothiadiazinone compounds by reacting a mixture of bromine and water with an inorganic cyanide and then with a salt of a 2,1,3-benzothiadiazin-4-one-2,2-dioxide and a base.

1 Claim, No Drawings

PREPARATION OF 1-CYANO-2,1,3-BENZOTHIADIAZINONES

The present invention relates to a process for the preparation of a 1-cyano-2,1,3-benzothiadiazinone compounds of the general formula I

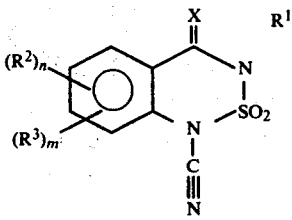

where
R¹ is alkyl, haloalkyl, cycloalkyl, alkenyl, alkynyl, haloalkenyl, halogenoalkynyl, alkoxyalkyl, alkylmercaptoalkyl, alkylcarbamoylalkyl and dialkylcarbamoylalkyl, alkoxycarbonyl, alkoxycarboalkyl, alkoxycarboalkenyl, alkanoylalkyl, aryl (which is unsubstituted or is substituted by halogen, methyl or halomethyl) or a heterocyclic ring,
R² and R³ independently of one another are halogen, nitro, lower alkyl, alkoxyalkyl, halo-lower alkyl, cycloalkyl, arylalkyl, aryl, CN, SCN, CO₂R⁴,

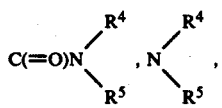

YR⁵, SO₂R⁴, SO₂OR⁴,

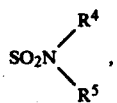

(C=O)R⁴ or Y'CF₂C(Z)₃,
R⁴ and R⁵ independently of one another are unsubstituted or halogen-, methyl- or nitro-substituted lower alkyl or aryl,
X, Y and Y' independently of one another are oxygen or sulfur,
each Z, independently of the others, is hydrogen or halogen and
n and m independently of one another are integers from 0 to 4, but m+n is not greater than 4,
by reacting an aqueous solution of a salt of the compound I with an inorganic cyanide and bromine.

The term "halogen" means fluorine, chlorine, bromine or iodine.

The terms "lower alkyl" and "halo-lower alkyl" denote branched or straight-chain unsubstituted or halogen-substituted alkyl with 1 to 6 carbon atoms.

The term "cycloalkyl" means, for example, cyclopropyl, cyclobutyl, cyclopentyl, cyclohexyl, cycloheptyl or alkyl-substituted cycloalkyl.

The term "aryl" means phenyl or substituted phenyl, e.g. halophenyl or tolyl.

R¹ can inter alia be hydrogen, methyl, ethyl, n-propyl, isopropyl, cyclopropyl, n-butyl, isobutyl, tert.-butyl, cyclobutyl, n-pentyl, pent-2-yl, pent-3-yl, tert.-amyl, neopentyl, 2-methylbutyl, 3-methyl-butyl, 3-methyl-but-2-yl, cyclopentyl, n-hexyl, 4-methyl-pent-2-yl, 2,3-dimethylbutyl, 2-methyl-pent-1-yl, hex-2-yl, hex-3-yl, 3-methyl-pent-2-yl, 3-methylpentyl, 4-methylpentyl, 3-methyl-pent-3-yl, 4,4-dimethylbutyl, cyclohexyl, heptyl, hept-2-yl, hept-3-yl, hept-4-yl, cycloheptyl, oct-1-yl, oct-2-yl, oct-3-yl, oct-4-yl, oct-5-yl, 5-ethyl-hept-2-yl, 2,6-dimethyl-hept-4-yl, 7-ethyl-2-methyl-non-4-yl, 2,4-dimethyl-pent-3-yl, 3-methylhept-2-yl, 5-ethyl-non-2-yl, nonyl, decyl, undecyl, dodecyl, tridecyl, tetradecyl, pentadecyl, hexadecyl, heptadecyl, octadecyl, nonadecyl, eicosyl, 6-ethyl-dec-3-yl, 6-ethyl-oct-3-yl, 2-methyl-pent-2-yl, 2,3-dimethyl-but-2-yl, 2-methyl-hex-2-yl, 3-ethyl-pent-3yl, 3-methyl-hex-3-yl, 2,3-dimethylpent-3-yl, 2,4-dimethyl-pent-2-yl, 2,2,3-trimethyl-but-3-yl, 2-methyl-hept-2-yl, 4-methyl-hept-4-yl, 2,4-dimethyl-hex-2-yl, 2-methyl-oct-2-yl, 1-methyl-cyclopent-1-yl, 1-methylcyclohex-1-yl, 1-ethyl-cyclohex-1-yl, chloro-tert.-butyl, 1,1-dichloro-2-methyl-prop-2-yl, 1,3-dichloro-2-methyl-prop-2-yl, 1-cyclohexyl-eth-1-yl, 1-chloroethyl, 2-chloroethyl, 1-chloropropyl, 2-chloropropyl, 3-chloropropyl, 1-chloro-prop-2-yl, 2chlorobutyl, 2chloro-2-methyl-prop-3-yl, 1-fluoroethyl, 2-fluoroethyl, 2-fluoropropyl, 3-fluoropropyl, 1-fluoro-prop-2-yl, 2-fluorobutyl, 2-fluoro-2-methyl-prop-3-yl, 2-bromoethyl, 3-bromopropyl, 4-chlorobutyl, 2-chlorocyclohexyl, 1,1,1-trifluoroisopropyl, hexafluoro-2-methylisopropyl, hexachloroisopropyl, 1,2-dibromo-allyl, 2,2,2-trifluoroethyl, 1-chloro-but-2-yn-4-yl, 3-chloro-but-1-yn-4-yl, 1-chloro-but-2-en-4-yl, 2,3-dibromo-prop-1-yl, 2,2,2-trichloroethyl, 1-chloropent-2-yn-4-yl, 2,2,2-tribromoethyl, 3,4,4-trichlorobut-3-en-2-yl, 1bromo-prop-2-yl, 1,3-dibromo-prop-2-yl, 3-chlorobut-1-en-4-yl, allyl, methallyl, crotyl, 2-ethylhex-2-en-1-yl, hex-5-en-1-yl, undec-10-en-1-yl, 2-methyl-but-2-en-1-yl, 2-methylbut-1-en-3-yl, but-1-yn-3-yl, but-2-yn-1-yl, but-1-en-3-yl, propargyl, 2-methylbut-1-en-4-yl, 2-methylbut-2-en-4-yl, 3-methylbut-1-en-3-yl, 1-ethynylcyclohexyl, methoxyethyl, ethoxyethyl, 3-methoxypropyl, methoxyisopropyl, 3-methoxybutyl, 1-methoxy-but-2-yl, ethoxy-tert.-butyl, methoxy-tert.-butyl, cyclohexoxy-tert.-butyl, 2-methoxy-butyl, 4-methoxy-butyl, methylmercapto-ethyl, ethylmercaptoethyl, 3-methyl-mercapto-propyl, 3-methylmercaptobutyl, 1-methylmercaptobutyl-2, methylmercapto-tert.-butyl, 2-methylmercaptobutyl, 4-methylmercaptobutyl, 3-n-butoxyethyl, 2-ethoxypropyl, 3-ethoxy-prop-2-yl, 2-methylbutan-3-on-2-yl, 2-methylpentan-4-on-2-yl, butan-3-on-1-yl, butan-3-on-2-yl, propan-2-on-1-yl, pentan-2-on-1-yl, methylacetate-2, ethyl-acetate-2, methyl-propionate-2, methylpropionate-3, methylbutyrate-2, methylbutyrate-3, methylbutyrate-4, methyl-(2-vinylpropionate-2), methyl-(2-vinylacetate-2), methylcarbamyl-methyl, dimethylcarbamyl-methyl, phenyl, o-tolyl, m-tolyl, p-fluorophenyl, m-fluorophenyl, p-chlorophenyl, p-tolyl, o-chlorophenyl, o,p-dichlorophenyl, o,p-difluorophenyl, m-trifluoromethylphenyl, o-fluorophenyl, 3,5-dimethylphenyl, 3,5-dichlorophenyl, p-bromophenyl, m-bromophenyl, 3,5-difluorophenyl, and pyrrolidinyl.

R² and R³ can independently of one another inter alia be fluorine, chlorine, bromine, iodine, nitro, methyl, ethyl, n-propyl, i-propyl, n-butyl, i-butyl, sec.-butyl, tert.-butyl, n-pentyl, pent-2-yl, pent-3-yl, tert.-amyl, neopentyl, 2-methylbutyl, 3-methylbutyl, 3-methyl-but-2-yl, cyclopentyl, n-hexyl, 4-methyl-pent-2-yl, 2,3-dimethylbutyl, 2-methyl-pent-1-yl, 2-hexyl, 3-hexyl, 3-methyl-pent-2-yl, 3-methylpentyl, 4,4-dimethylbutyl, cyclohexyl, methoxyethyl, 3-methoxypropyl, methoxyisopropyl, chloromethyl, trichloromethyl, trifluoromethyl, difluoromethyl, fluoromethyl, iodomethyl, (3',4'-dichloro)-phenylmethyl, benzyl, o-tolyl, p-fluorophenyl, p-bromophenyl, m-chlorophenyl, cyano, thiocyanato, methoxycarbonyl, isopropoxycarbonyl, ethoxycarbonyl, N-methyl-N-phenyl-aminocarbonyl, dimethylaminocarbonyl, methylethyl-aminocarbonyl, diethylaminocarbonyl, diisopropylaminocarbonyl, p-chlorophenyl-methyl-aminocarbonyl, dimethylamino, diethylamino, diisopropylamino, methoxy, ethoxy, isopropoxy, trifluoromethoxy, methylsulfonyl, phenylsulfonyl, isopropylsulfonyl, methoxysulfonyl, ethoxysulfonyl, isopropoxysulfonyl, dimethylaminosulfonyl, diethylaminosulfonyl, piperidinosulfonyl, methylcarbonyl, ethylcarbonyl, isopropylcarbonyl, tert.-butylcarbonyl, p-fluorophenylcarbonyl, (4'-trifluoromethyl-2'-nitro)-phenylcarbonyl, 1',1',2',2'-tetrfluoroethoxy, 2',2',2'-trichloroethoxy, 2'-chloro-2',2'-difluoro-1',1'-difluoroethoxy, methylthio, propylthio, isopropylthio and tert.-butylthio.

It is known from German Laid-Open Application DOS No. 2,656,289 that a benzothiadiazinone compound of the formula I may be prepared by reacting a compound of the general formula II

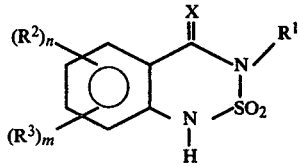

where $R^1$, $R^2$, $R^3$, X, m and n have the above meanings, with a compound of the general formula III

   Hal—C≡N   III where Hal is Cl or Br, in the presence or absence of an acid-binding agent and in the presence or absence of an inert solvent, or by reacting a salt of a compound of the formula II with a compound of the formula III, in the presence or absence of an inert solvent.

Though this process gives the desired products in satisfactory yield if carried out on a laboratory scale, very great problems arise when this reaction is transferred to an industrial scale.

For example, cyanogen bromide and cyanogen chloride cannot be purchased and transported in substantial amounts at a time, because of the hazards entailed in the transport.

Furthermore, the instability of these compounds (G. Sorbe, Giftige und explosive Substanzen, page 46, UmschauVerlag, Frankfurt/Main, 1968) rules out storage of the cyanogen halides before the reaction.

In particular, when using the cyanogen halides on an industrial scale, the exceptional toxicity of these compounds demands strictest safety measures, which make the process complicated and involved to carry out. The bases used in the conventional process, if they are organic compounds, can react with cyanogen halides under certain conditions and give undesirable by-products, so that the yields can decrease greatly, especially when compounds of the general formula II which react sluggishly are reacted with cyanogen halides. If inorganic bases are used as acid-binding agents, or if salts of the compounds of the formula II are used, the starting compounds are in part in solid form, because of the low solubility of these compounds in the inert solvents mentioned, and during the reaction inorganic halides additionally precipitate in solid form and on the one hand enclose or encapsulate the starting compounds which may also be sparingly soluble in the inert solvent, thereby withdrawing these compounds from the reaction, or, on the other hand, interfere with the working up of the reaction mixture and the isolation of the end product.

Finally, the desired end products are obtained as solutions in the above inert solvents, from which they have to be isolated with considerable effort and with the expenditure of a large amount of energy. Furthermore, the organic solvents must be recovered virtually quantitatively, in order to protect the environment.

We have found, surprisingly, that all these difficulties in the preparation of compounds of the formula I are avoided by a method wherein a solution of an about equimolar amount of an inorganic cyanide in water is added to a mixture of bromine and water, preferably at from −5° to +50° C., thereafter an aqueous solution of an at most equimolar amount of a salt of a compound of the formula II with a base is added, the batch is mixed thoroughly, preferably until no further end product precipitates from the mixture, and the end product formed is isolated from the mixture.

Preferably, the reaction is carried out at room temperature (20° C.). However, it can also be carried out at elevated temperatures (from 20° to 50° C.). The inorganic cyanide used can be potassium cyanide or preferably sodium cyanide. The salt of the compound II with a base can be the potassium salt or preferably the sodium salt. The end product can, for example, be extracted from the reaction mixture in the liquid form by means of an organic solvent, for example dichloroethane, or can, preferably, be isolated in the solid form by filtering off, decanting or syphoning off the mother liquid. Thorough mixing of the reaction batch is achieved, for example, by vigorous stirring.

In a preferred embodiment, an equimolar amount of a solution of an alkali metal cyanide in water is added dropwise to an emulsion or solution of bromine in water at from 0° to 5° C. until the bromine is completely decolorized, 0.5 to 1 mole equivalent of a solution of a 2,1,3-benzothiadiazine compound of the formula II, dissolved in an equimolar amount of dilute aqueous alkali metal hydroxide solution, is then added, and thereafter the procedure is continued as described above.

If desired, the aqueous alkaline solution of the particular 2,1,3-benzothiadizin-4-one compound of the formula II, as obtained from the conventional industrial preparation of this compound, can, after neutralization of any excess alkali with acid, be used directly, without prior isolation of the 2,1,3-benzothiadiazine compound of the formula II, for the process according to the invention.

The process according to the invention is exceptionally simple and can be carried out without any organic solvents wich would have to be recovered or destroyed after completion of the reaction, and the use of which would entail additional safety measures. It is particularly advantageous that the reaction starts from an inorganic cyanide and bromine, which are easily handled chemicals, and that the reactants can be introduced in the liquid state into a closed apparatus, so that contact of personnel with the extremely toxic cyanogen bromide is virtually impossible. Be avoiding the storage, transportation and handling of a cyanogen halide, the process according to the invention is far superior to the conventional method.

Surprisingly, the process according to the invention entails virtually no side reactions, so that even on reacting compounds of the general formual II which react sluggishly and require fairly long reaction times or fairly high reaction temperatures, the cyano compounds of the formula I are obtained in very good yield, whilst in the preparation by the conventional method the yields are only moderate. For example, 8-chloro-1-cyano-3-isopropyl-2,1,3-benzothiadiazin-4-one-2,2-dioxide can only be obtained in about 30 percent yield by the process described in German Laid-Open Application DOS No. 2,656,289, whilst it can be obtained in about 95 percent yield by the process according to the invention (compare Example 4).

The novel process also provides a substantial advance in respect of the requirements of environmental protection. Because of the very good yields, only small amounts of organic by-products are formed and these can, if necessary, be extracted from the mother liquor with small amounts of organic solvents. The reaction product sodium bromide, present in the aqueous solution, is a compound widely encountered in nature and does not pollute the environment. Unconsumed cyanogen bromide present in the aqueous solution can be decomposed rapidly and completely by adding at least two moles, per mole of cyanogen bromide, of a basic compound, for example sodium hydroxide solution, sodium carbonate solution or, preferably, ammonia or an aqueous solution of ammonia, the basic compound being added before or after the isolation of the end product. The decomposition of cyanogen bromide with ammonia results in ammonium bromide, which is neutral to the environment, and cyanamide, known, in the form of its salts, as a plant nutrient. The cyanamide is ultimately converted by water, via urea, to ammonium bicarbonate. If, for example, sodium hydroxide solution is used to decompose any excess cyanogen bromide, the compounds formed are sodium bromide and sodium cyanate, and the latter is very rapidly degraded by water to ammonium bicarbonate. The latter salt is neutral to the environment and has, for example, been used for many years under the trivial name of hartshorn salt as a constituent of domestic baking powder.

As stated above, the compound of the formula I prepared by the process according to the invention precipitates as a solid from the aqueous solution and can be filtered off. If, however, the end product is subsequently to be dissolved in an organic solvent and be reused, or employed, in this form, it can of course also be directly extracted with this solvent from the aqueous reaction mixture. In such a case, the organic solvent can be added at any point in time after the addition of the inorganic cyanide, provided that this solvent does not react with cyanogen bromide or with another reactant.

In the process according to the invention, the inorganic cyanides used can be any cyanides which in aqueous solution form cyanide ions, preferably cyanides of metals of the first and second groups of the periodic table of the elements, especially sodium cyanide and potassium cyanide.

A plurality of bases can be used to prepare the salts of the 2,1,3-benzothiadiazin-4-one-2,2-dioxides, provided that with the exception of the anions of the 2,1,3-benzothiadiazin-4-one-2,2-dioxides, all the neutralization products, for example the cations or weak acids formed, are inert toward cyanogen bromide. Particularly suitable bases are therefor the hydroxides, bicarbonates and carbonates of the alkali metals and alkaline earth metals, especially sodium hydroxide, potassium hydroxide, calcium hydroxide, magnesium hydroxide, barium hydroxide, sodium bicarbonate, potassium bicarbonate, sodium carbonate, potassium carbonate, magnesium carbonate, calcium carbonate and barium carbonate.

The reactions can be carried out either at low temperatures (for example from $-5°$ to $19°$ C.), in which case the crystallization of water imposes a natural lower limit, or at room temperature ($20°$ C.) or elevated temperatures (for example from $21°$ to $50°$), with the volatility of cyanogen bromide imposing a natural upper limit on the temperature. However, by working under superatmospheric pressure (for example from 1 to 5 bar) the reaction can also be carried out at higher temperatures (for example at from $50°$ to $100°$ C.). In total, it is thus possible to work, for example, within a range of from $-5°$ to $+100°$ C.

The Examples which follow illustrate how the process according to the invention may be carried out, and show its advantages over the conventional process. However, the process according to the invention is not restricted to these Examples.

EXAMPLE 1

A solution of 19.5 parts by weight of potassium cyanide in 180 parts by weight of water is added dropwise, at from $0°$ to $5°$ C., to a well-stirred emulsion of 48 parts by weight of bromine in 90 parts by weight of water. A solution of 48 parts by weight of 3-isopropyl-1H-2,1,3-benzothiadiazin-4-3H-one-2,2-dioxide and 18.5 parts by weight of sodium bicarbonate in 240 parts by weight of water is added dropwise and the mixture is stirred for 36 hours at room temperature ($20°$ C.). The precipitate formed is filtered off, washed with water and dried to give 48.2 parts by weight of 1-cyano-3-isopropyl-1H-2,1,3-benzothiadiazin-4-3H-one-2,2-dioxide of melting point $99°-101°$ C.

EXAMPLE 2

A solution of 1,470 parts by weight of sodium cyanide in 5,000 parts by weight of water is added dropwise, at from $0°$ to $5°$ C., to a well-stirred emulsion of 4,800 parts by weight of bromine in 24,000 parts by weight of water. A solution of 800 parts by weight of sodium hydroxide and 5,080 parts by weight of 3-isopropyl-8-methyl-1H-2,1,3-benzothiadiazin-4-3H-one-2,2-dioxide in 20,000 parts by weight of water is added and the mixture is stirred for 48 hours at room temperature ($20°$ C.). 800 parts by weight of 25 percent strength ammonia solution are then added, the mixture is stirred for not more than 10 minutes at room temperature and the precipitate is filtered off and washed with water. After drying, 5,320 parts by weight of 1-cyano-3-isopropyl-8-methyl-1H-2,1,3-benzothiadiazin-4-3H-one-2,2-dioxide of melting point $104°$ C. are obtained.

EXAMPLE 3

(a) Conventional Process (Prior Art)

24 parts of 3-isopropyl-2,1,3-benzothiadiazin-4-one-2,2-dioxide are suspended in 150 parts of 1,2-dichloroethane and 12 parts of cyanogen bromide are added at $5°-10°$ C. 14 parts of N,N-dimethylcyclohexylamine are then added dropwise at the same temperature and the mixture is stirred for 4 hours at room temperature ($20°$ C.). The solution is then washed twice with water and twice with cold normal aqueous sodium hydroxide solution, and is dried, and the solvent is removed under reduced pressure. After recrystallizing the residue from isopropanol, 22 parts of 1-cyano-3-isopropyl- 2,1,3-benzothiadiazin-4-one-2,2-dioxide of melting point 100°–101° C. are obtained.

(b) Novel Process (According to the Invention)

5.4 parts of sodium cyanide in 40 parts of water are added dropwise to 17.6 parts of bromine in 150 parts of water at from 5° to 10° C. A solution of 24 parts of 3-isopropyl-2,1,3-benzothiadiazin-4-one-2,2-dioxide and 4 parts of sodium hydroxide in 100 parts of water is then added and the mixture is stirred for 2 hours at 50° C. When it has cooled, the precipitate is filtered off and dried. 25 parts of 1-cyano-3-isopropyl-2,1,3-benzothiadiazin-4-one-2,2-dioxide of melting point 99°–101° C. are obtained.

EXAMPLE 4

(a) Conventional Process (Prior Art)

127 parts of cyanogen bromide are added to 274.5 parts of 8-chloro-3-isopropyl-2,1,3-benzothiadiazin-4-one-2,2-dioxide dissolved in 1,500 parts of 1,2-dichloroethane at 5°–10° C. and 121 parts of triethylamine are then added dropwise at the same temperature. The reaction mixture is then stirred for 48 hours at room temperature (20° C.), after which it is washed twice with water and three times with normal aqueous sodium hydroxide solution and dried, and the solvent is evaporated off under reduced pressure. The residue is recrystallized twice from isopropanol and gives 90 parts of 8-chloro-1-cyano-3-isopropyl-2,1,3-benzothiadiazin-4-one-2,2-dioxide of melting point 123°–124° C.

(b) Novel Process (According to the Invention)

A solution of 54 parts of sodium cyanide in 400 parts of water is added dropwise to 176 parts of bromine in 1,500 parts of water at 5°–10° C. A solution of 274.5 parts of 8-chloro-3-isopropyl-2,1,3-benzothiadiazin-4-one-2,2-dioxide and 40 parts of sodium hydroxide in 1,000 parts of water is then added and the mixture is stirred for 12 hours at room temperature (20° C.). After filtering off and drying the precipitate, 280 parts of 8-chloro-1-cyano-3-isopropyl-2,1,3-benzothiadiazin-4-one-2,2-dioxide of melting point 123°–124° C. are obtained.

We claim:

1. A process for the preparation of a 1-cyano-2,1,3-benzothiadiazin-4-one-2,2-dioxide of the general formuala I

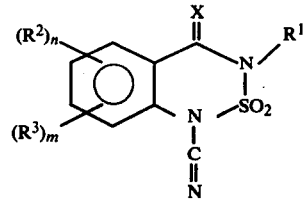

where
$R^1$ is alkyl, haloalkyl, cycloalkyl, alkenyl, alkynyl, haloalkenyl, halogenoalkynyl, alkoxyalkyl, alkylmercaptoalkyl, alkylcarbamoylalkyl and dialkylcarbamoylalkyl, alkoxycarbonyl, alkoxycarboalkyl, alkoxycarboalkenyl, alkanoylalkyl, aryl (which is unsubstituted or is substituted by halogen, methyl or halomethyl) or a heterocyclic ring,
$R^2$ and $R^3$ independently of one another are halogen, nitro, lower alkyl, alkoxyalkyl, halo-lower alkyl, cycloalkyl, arylalkyl, aryl, CN, SCN, $CO_2R^4$,

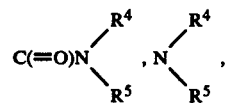

$YR^5$, $SO_2R^4$, $SO_2OR^4$,

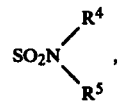

$(C=O)R^4$ or $Y'CF_2C(Z)_3$,
$R^4$ and $R^5$ independently of one another are unsubstituted or halogen-, methyl- or nitro-substituted lower alkyl or aryl,
X, Y and Y' independently of one another are oxygen or sulfur,
each Z, independently of the others, is hydrogen or halogen and
n amd m independently of one another are integers from 0 to 4, but m+n is not greater than 4, wherein an about equimolar amount of an inorganic cyanide, dissolved in water, is added to a mixture of bromine and water, an aqueous solution of an at most equimolar amount of a salt of a 2,1,3-benzothiadiazin-4-one-2,2-dioxide of the formula II

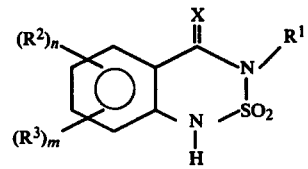

where $R^1$, $R^2$, $R^3$, n, m and X have the above meanings, and of a base is then added, the batch is mixed thoroughly and the resulting end product is isolated from the mixture.

* * * * *